(12) United States Patent
Inman

(10) Patent No.: US 7,156,654 B2
(45) Date of Patent: Jan. 2, 2007

(54) SELF-LOCKING POWER COMPONENT FOR ORTHODONTIC APPLIANCES

(76) Inventor: Donal P. Inman, 9381 W. Sample Rd., Coral Springs, FL (US) 33065

(*) Notice: Subject to any disclaimer, the term of this patent is extended or adjusted under 35 U.S.C. 154(b) by 224 days.

(21) Appl. No.: 10/824,979

(22) Filed: Apr. 14, 2004

(65) Prior Publication Data

US 2004/0265769 A1 Dec. 30, 2004

Related U.S. Application Data

(60) Provisional application No. 60/462,839, filed on Apr. 16, 2003.

(51) Int. Cl.
*A61C 3/00* (2006.01)
(52) U.S. Cl. ............................................. 433/7; 433/21
(58) Field of Classification Search ............... 433/21, 433/6–7, 18–19, 23–24
See application file for complete search history.

(56) References Cited

U.S. PATENT DOCUMENTS

| | | | | |
|---|---|---|---|---|
| 4,571,178 A | * | 2/1986 | Rosenberg | 433/18 |
| 5,785,520 A | * | 7/1998 | Carano et al. | 433/7 |
| 6,220,856 B1 | * | 4/2001 | Carano et al. | 433/7 |
| 6,267,589 B1 | * | 7/2001 | Farzin-Nia et al. | 433/7 |

* cited by examiner

*Primary Examiner*—Cris L. Rodriguez
*Assistant Examiner*—Candice C. Stokes
(74) *Attorney, Agent, or Firm*—Hodgson Russ LLP

(57) ABSTRACT

A force adjusting mechanism for an orthodontic appliance wherein the appliance functions to move teeth and/or to expand the dental arch. The mechanism includes a shaft operatively coupled at opposite ends between a first portion of the appliance which is anchored in the patient's dental arch and a second portion of the appliance which applies force to one or more of the patient's teeth. A lock is slidable along the shaft to compress a spring between the lock and the second portion of the appliance. Co-operating structures on the shaft and on the lock provide a unidirectional ratchet movement of the lock along the shaft. Thus, the lock may be advanced one step at a time in one direction only, preferably manually using an implement for engaging the lock, to compress the spring to apply force to one or more of the patient's teeth. Advantageously, this may be done by the patient or a parent or guardian without the need for an office visit to a clinician. The cooperating structures can include a series of successive detent formations along the shaft and a component on the lock moveable into and out of the detent formations thereby avoiding thread stripping or slippage.

10 Claims, 8 Drawing Sheets

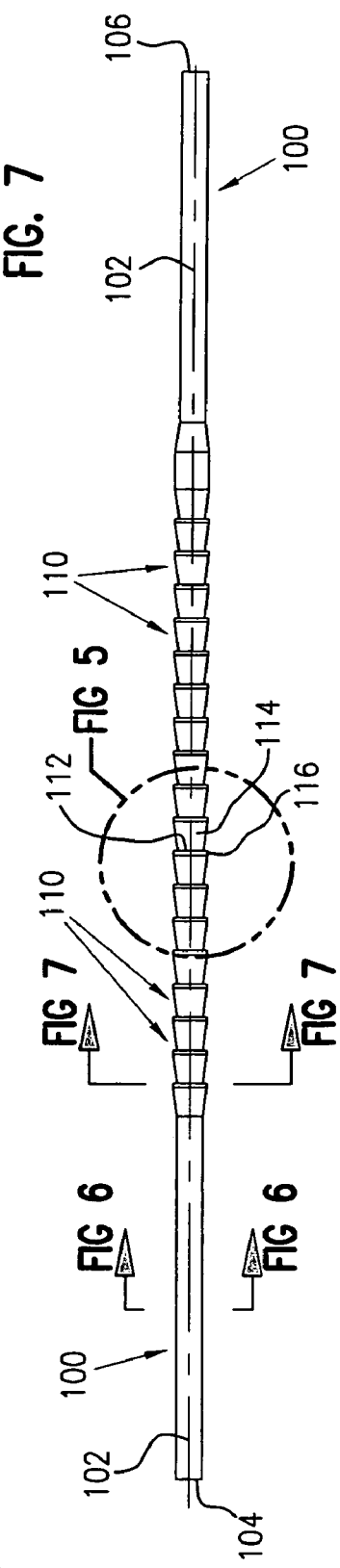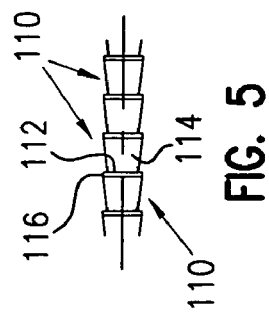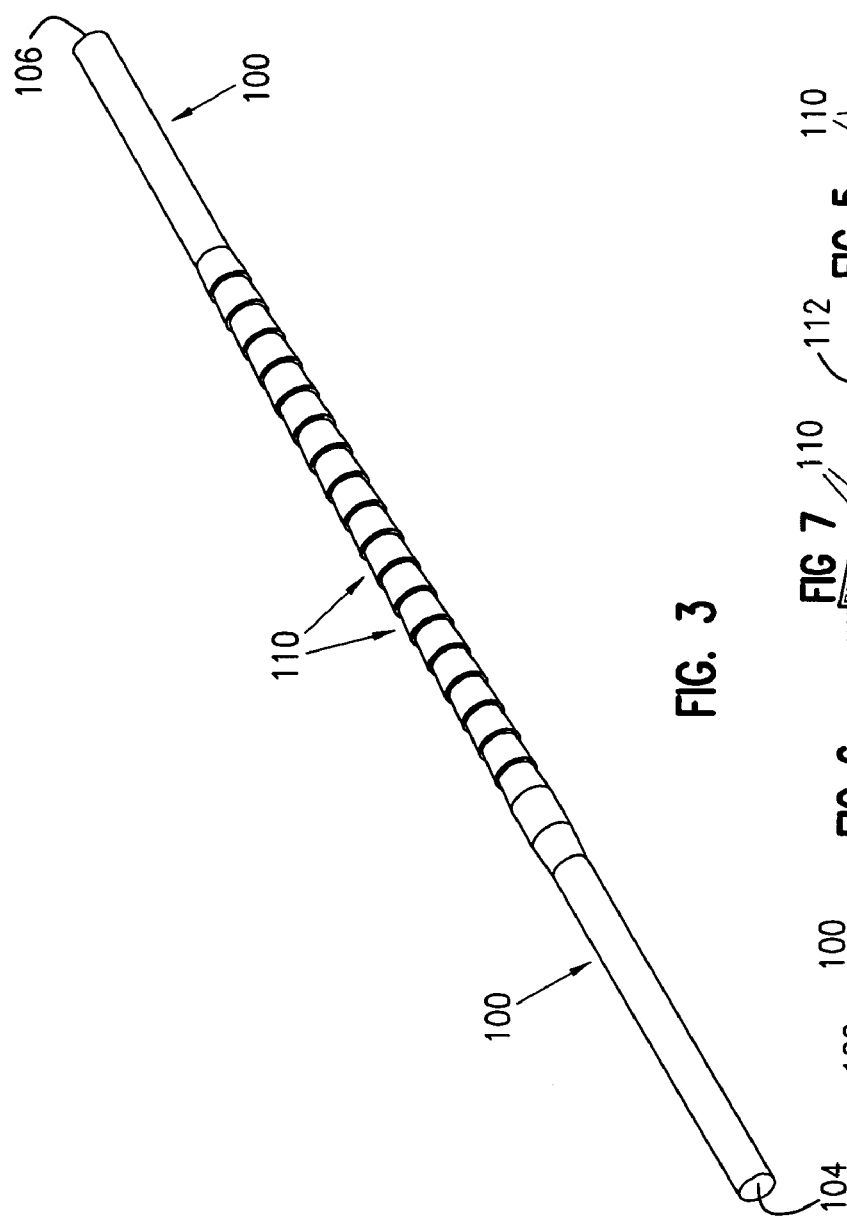

US 7,156,654 B2

SELF-LOCKING POWER COMPONENT FOR ORTHODONTIC APPLIANCES

CROSS-REFERENCE TO A RELATED APPLICATION

Applicant claims priority based on U.S. provisional patent application No. 60/462,839 filed Apr. 16, 2003 and entitled "S.L.P.M Self-Locking Power Module", the disclosure of which is hereby incorporated by reference.

BACKGROUND OF THE INVENTION

This invention relates to the art of orthodontic appliances and methods, and more particularly to a new and improved force adjusting mechanism and method of operating the same for use in orthodontic appliances.

Various orthodontic appliances have mechanisms or components which provide force for moving teeth and/or expanding the dental arches. During the course of treatment, as the teeth are moved toward the desired position/location, it is necessary periodically to adjust the mechanisms/components so that the required amount of force is continued to be applied to the teeth. Such force applying arrangements heretofore available have a number of limitations such as being cumbersome in design, being subject to failure caused by screw thread stripping or slipping and providing limited access to adjustment components due to intra-oral environment. All of these arrangements have the added disadvantage of requiring adjustment by a clinician thereby necessitating an office visit for each adjustment.

It would, therefore, be highly desirable to provide a force adjusting mechanism for orthodontic appliances which is effective and reliable in operation and which is easy to adjust by the patient or a parent or guardian without the need for an office visit to a clinician.

The invention provides a force adjusting mechanism for an orthodontic appliance wherein the appliance functions to move teeth and/or to expand the dental arch. The mechanism includes a shaft operatively coupled at opposite ends between a first portion of the appliance which is anchored in the patient's dental arch and a second portion of the appliance which applies force to one or more of the patient's teeth. A lock is slidable along the shaft to compress a spring between the lock and the second portion of the appliance. Cooperating structures on the shaft and on the lock provide a unidirectional ratchet movement of the lock along the shaft. Thus, the lock may be advanced one step at a time in one direction only, preferably manually using an implement for engaging the lock, to compress the spring to apply force to one or more of the patient's teeth. Advantageously, this may be done by the patient or a parent or guardian without the need for an office visit to a clinician. The cooperating structures can include a series of successive detent formations along the shaft and a component on the lock moveable into and out of the detent formations thereby avoiding thread stripping or slippage.

The foregoing and additional advantages and characterizing features of the invention will become clearly apparent upon a reading of the ensuing detailed description together with the included drawing.

BRIEF DESCRIPTION OF THE DRAWING FIGURES

FIG. 3 is a perspective view of the shaft of the force adjusting mechanism of the invention;

FIG. 4 is an enlarged side elevational view of the shaft of FIG. 3;

FIG. 5 is a fragmentary enlarged elevational view taken in the outline designated 5—5 in FIG. 4;

FIG. 6 is a sectional view taken about on line 6—6 in FIG. 4;

FIG. 7 is a sectional view taken about on line 7—7 in FIG. 4;

DETAILED DESCRIPTION OF THE INVENTION

Figure 1:
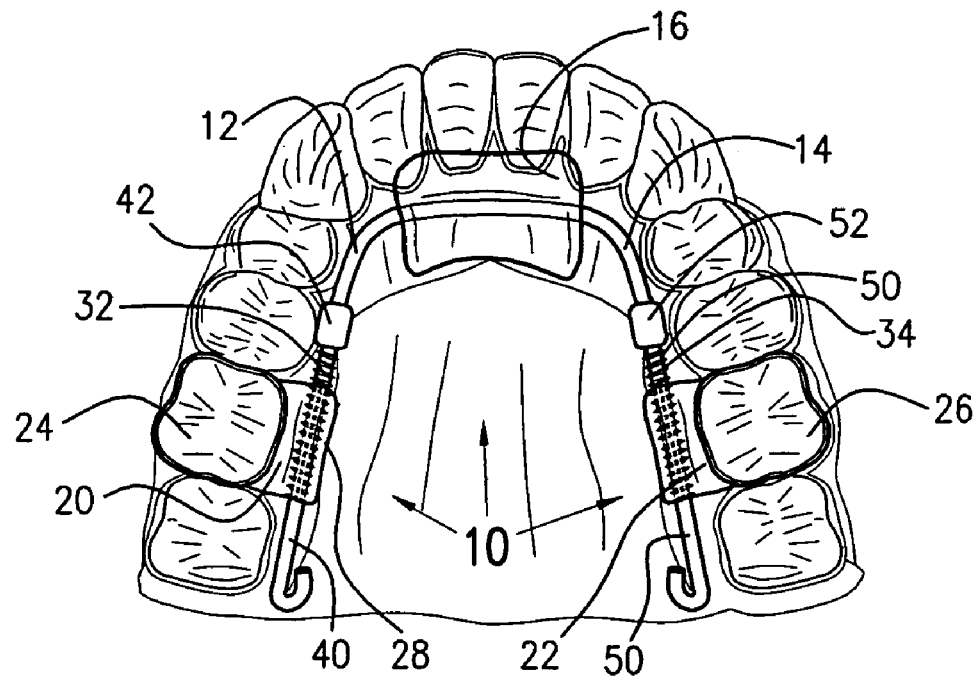
FIG. 1 is a perspective view of one form of orthodontic appliance including the force adjusting mechanism of the invention.

The force adjusting mechanism of the present invention is readily incorporated in and highly effective in a wide variety of orthodontic appliances, one of such appliances being designated 10 in FIG. 1. Appliance 10 is representative of a number of types of orthodontic appliances which apply force to a patient's teeth in a direction generally longitudinally of the dental arch, i.e. in a direction extending between the front and rear of the dental arch. Appliance 10 includes a first portion which is anchored or supported in the patient's dental arch. Members 12 and 14 of the appliance frame are secured in a plate-like component 16 of plastic or like material which abuts the inner surfaces of the patient's front teeth and the adjacent tissue. Appliance 10 has a second portion including spring means which applies force to one or more of the patient's teeth. A pair of bands 20 and 22 are attached to molar teeth 24 and 26, respectively, in a known manner. Band 20 has an integral boss 28 and band 22 has an integral boss 30, and both bosses 28 and 30 are located on the lingual sides of the bands. A first spring 32 is located with one end thereof abutting boss 28 of band 20, and a second spring 34 is located with one end thereof abutting boss 30 of band 22.

The force adjusting mechanism of the invention is provided in duplicate in the illustrative appliance 10 shown in FIG. 1, there being one on each side of the appliance, i.e. one for adjusting the force applied to each molar 24 and 26. Referring first to the one on the left-hand side of appliance 10 as viewed in FIG. 1, the force adjusting mechanism of the invention includes a shaft 40 operatively coupled at opposite ends thereof between the first and second portions of appliance 10. One end of shaft 40 is connected to frame portion 12, for example by being fixedly received in a hollow open end of frame portion 12. The other end of shaft 40 extends through spring 32 and boss 28. A lock 42 is movable along shaft 40 to compress spring 32 between lock 42 and boss 28. Co-operating structures on shaft 40 and lock 42, which will be described in detail presently, provide a unidirectional ratchet movement of lock 42 on shaft 40. As a result, lock 42 may be advanced one step at a time, in one direction only, to compress spring 32 to apply force in a stepwise manner to the molar tooth 24 during the course of the treatment period as tooth 24 is moved toward the desired position/location. In the operation of the illustrative appliance 10, force is applied to molar teeth 24 to move it in a direction toward the rear of the patient's dental arch.

The force adjusting mechanism of the invention on the right-hand side of appliance 10 as viewed in FIG. 1 has an identical shaft 50 and lock 52 which are installed in the appliance and which function in a manner identical to that of shaft 40 and lock 42. However, molar 26 may require a different amount of movement in which case spring 34 may have a different force rating or spring constant as compared to that of spring 32 and lock 52 may be adjusted at different times compared to that of lock 42.

Locks 42 and 52 are readily and easily adjusted, i.e. moved incrementally or step-by-step, along the respective shafts 40 and 50. This is done manually, using a suitable instrument or tool which will be described in detail presently. Advantageously, the adjustment of locks 42 and 52 can be done by the patient or by the patient's parent or guardian. The unidirectional ratchet movement of the lock along the shaft prevents any confusion in the manner in which the adjustment is to be made and assures that the adjustment is made in the proper direction, i.e. always in a direction compressing the spring.

Figure 2:
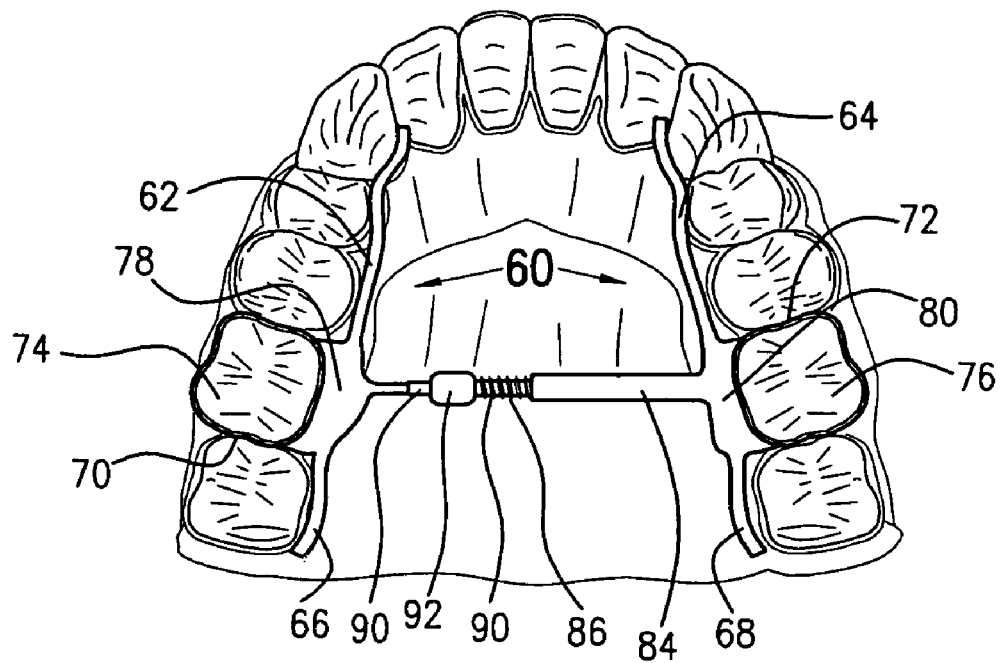
FIG. 2 is a perspective view of another form of orthodontic appliance including the force adjusting mechanism of the invention.

Referring now to FIG. 2 there is shown another form of orthodontic appliance 60 in which the force adjusting mechanism of the invention is readily incorporated and highly effective. Appliance 60 is representative of a number of types of orthodontic appliances which apply force to expand the dental arch of a patient, such appliances often called palatal expanders. Appliance 60 includes a first portion which is anchored or supported in the patient's dental arch. The appliance frame includes a first pair of rod-like portions 62 and 64 contacting the inner surfaces of teeth on opposite sides of the dental arch extending toward the front of the arch, and a second pair of relatively shorter, rod-like portions 66 and 68 contacting teeth on opposite sides at the rear of the dental arch. Appliance 60 has a second portion including spring means which applies force to one or more of the patient's teeth. A pair of bands 70 and 72 are attached to molar teeth 74 and 76, respectively, on opposite sides of the dental arch and in a known manner. Band 70 is secured, such as by soldering, to a junction 78 of frame portions 62 and 66, and band 72 is secured, such as by soldering, to a junction 80 of frame portions 64 and 68. A hollow tube 84 is attached at one end, such as by soldering, to one of the bands, in this illustration to band 72, and extends laterally of the patient's arch and terminates at a location approximately midway between the sides of the arch. A spring 86 is located with one end thereof abutting the end of tube 84.

The force adjusting mechanism of the invention includes a shaft 90 operatively coupled at opposite ends between the first and second portions of appliance 60. One end of shaft 90 is connected, such as by soldering, to the junction 78 of appliance frame portions 62 and 66 adjacent band 70. The other end of shaft 90 extends through spring 86 and tube 84. A lock 92 is movable along shaft 90 to compress spring 86 between lock 92 and tube 84. Co-operating structures on shaft 90 and lock 92, which will be described in detail presently, provide a unidirectional ratchet movement of lock 92 on shaft 90. As a result, lock 92 may be advanced one step at a time, in one direction only, to compress spring 86 to apply force in a stepwise manner between molar teeth 74 and 76. In the operation of the illustrative appliance 60, force is applied between molar teeth 74 and 76 in a manner expanding the teeth of the patient's dental arch.

Lock 92 is readily and easily adjusted, i.e. moved incrementally or step-by-step, along the shaft 90. This is done manually, using a suitable tool or instrument which will be described in detail presently. Advantageously, the adjustment of lock 92 can be done by the patient, or by the patient's parent or guardian. The unidirectional ratchet movement of the lock along the shaft prevents any confusion in the manner in which the adjustment is to be made and assures that the adjustment is made in the proper direction, i.e. always in a direction compressing the spring.

The particular appliances 10 and 60 shown in FIGS. 1 and 2 are merely illustrative of different types of orthodontic appliances in which the force adjusting mechanism of the invention can be incorporated. It is to be understood that the force adjusting mechanism of the invention likewise is readily incorporated and highly effective in many other types and varieties of orthodontic appliances.

FIGS. 3–7 show a preferred form of the shaft of the force adjusting mechanism of the invention. While shaft 100 shown in FIGS. 3–7 is circular in cross-section, the shaft in the force adjusting mechanism of the invention can have other shapes, such as square, rectangular, triangular and oval to mention a few. Shaft 100, which is representative of shafts 40, 50 and 90 in the mechanisms shown in FIGS. 1 and 2, is in the form of an elongated rod having a longitudinal axis 102 and opposite end faces 104 and 106. In a region substantially centered between ends 104 and 106 there is provided a series of successive detent formations 110. The detent formations 110 co-operate with one or more structures on the lock of the force adjusting mechanism of the invention, in a manner which will be described, to provide the unidirectional ratchet movement of the lock along the shaft previously mentioned. In the illustrative shaft shown the detent formations 110 are axially adjacent along the central portion of shaft 100 and each formation is generally frustoconical in shape. This, in turn, defines an annular shoulder 112 and an annular ramp-like surface 114 having an increasing diameter proceeding in an axial direction away from the shoulder. In this illustration, the detent formations 110 are identical in size and shape so that there is a series of shoulders 112 at equally axially spaced locations along the central portion of shaft 100 and, likewise, a series of ramp surfaces 114 at equally axially spaced locations along the central portion of shaft 100. In order to avoid sharp edges, the outer end of each ramp surface 114 meets shoulder 112 in an annular transition surface 116 of short axial length.

By way of example, in an illustrative force adjusting mechanism, shaft 100 can be of 316 stainless steel, the diameter measured at end faces 104, 106 can be about 0.035 inch, the length measured between end faces 104 and 106 can be about 2.36 inches, the axial length of the central portion of shaft 100 containing detent formations 110 can be about 0.860 inch, each detent formation 110 can have an axial length of about 0.045 inch, the surface 114 can have an inner or minimum diameter of about 0.035 inch and an outer or maximum diameter of about 0.045 inch and ramp surface 114 can define an angle of about 7.1 degrees with respect to the shaft longitudinal axis 102, and each annular transition surface 116 can have an axial length of about 0.005 inch. The foregoing is by way of example, for purposes of illustration, and shaft 100 can be of other materials, cross-sectional shapes and dimensions and detent formations 110 can be of other shapes and dimensions.

Figure 8:
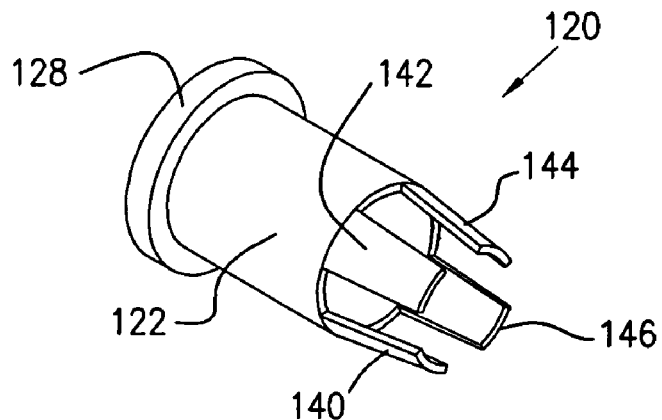
FIG. 8 is a perspective view of the lock of the force adjusting mechanism of the present invention.
Figure 9:
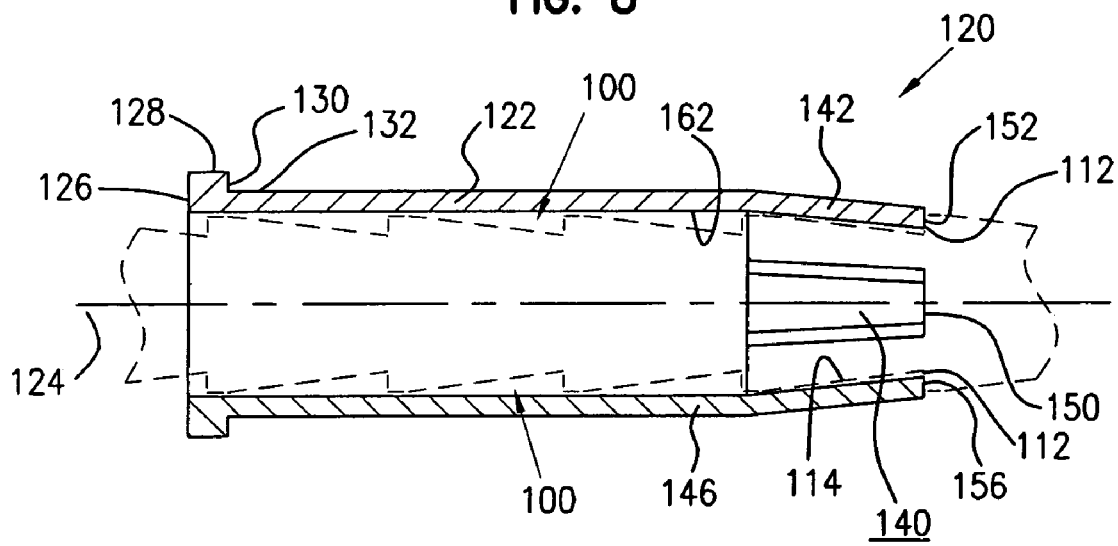
FIG. 9 is an enlarged longitudinal cross-sectional view of the lock of FIG. 8.
Figure 10:
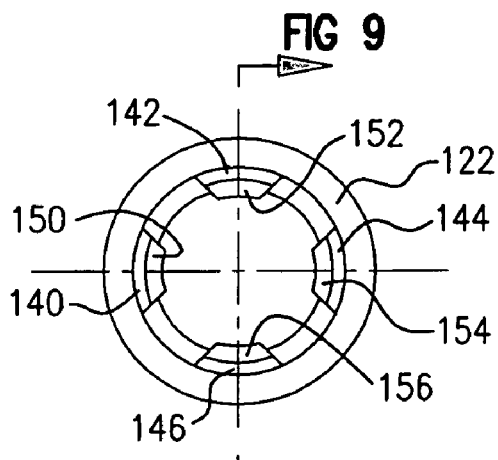
FIG. 10 is an end elevational view of the lock of FIG. 9.

FIGS. 8–10 show a preferred form of the lock of the force adjusting mechanism of the invention. As previously described, the lock is movable along the shaft and co-operating structures on the shaft and on the lock provide a unidirectional ratchet movement of the lock along the shaft, i.e. the lock may be advanced along the shaft one step at a time in one direction only. The cooperating structures include the series of detent formations 110 on shaft 100 and a component on the lock movable into and out of the detent formations 110 as the lock is advanced or indexed along shaft 100. Lock 120 shown in FIGS. 8–10 is in the form of a hollow body which receives shaft 100 therein. In particular, lock 120 includes a main body portion 122 in the form of a sleeve having substantially constant inner and outer diameters and a longitudinal axis 124. Body 122 terminates at one axial end 126, i.e. the left-hand end as viewed in FIG. 9, in an annular rim 128 which defines a ledge or shoulder 130 adjacent the outer surface 132 of body 122 for a purpose to be described. In the lock 120 shown in FIGS. 8–10 the component moveable into and out of the shaft detent formations comprises one or more flexible and/or resilient fingers located at the opposite axial end of body 122 and extending slightly inwardly toward the longitudinal axis 124. In the illustrative lock 120 shown in FIGS. 8–10 there are four fingers 140, 142, 144 and 146 located at substantially equal angular locations about the circumference of body 122. Each finger in the lock shown is substantially rectangular in shape with the sides thereof tapering slightly inwardly in an axial direction away from main body 122, each finger is of a length approximately one-quarter the overall axial length of lock 120, and the axial end faces 150, 152, 154 and 156 of the fingers are disposed substantially in a plane perpendicular to the lock longitudinal axis 124. The thickness of each finger 140, 142, 144 and 146 in the lock shown is the same as the wall thickness of main body portion 122, and each finger extends inwardly, and in a direction axially away from main body portion 122, to define a small acute angle with respect to the lock longitudinal axis 124.

The manner in which lock 120 is operatively associated with shaft 100 is illustrated diagrammatically in FIG. 9 wherein a portion of shaft 100 including detent formations 110 is shown in broken lines. Lock 120 is shown in a stationary position on shaft 100 where one or more fingers, here all four fingers 140, 142, 144 and 146 are received in one of the detent formations 110 and the corresponding axial end faces 150, 152, 154 and 156 are disposed toward and are located closely adjacent a shoulder 112 of that detent formation. The main body 122 of lock 120 extends axially along and over one or more detent formations 110 extending in a direction axially away from the detent formation in which the fingers have entered. The annular transition surfaces 116 between detent formations are slidably or movable received within the inner surface 162 of lock body 122.

It is apparent from the illustration of FIG. 9 that lock 120 cannot be moved further along shaft 100 to the right as viewed in FIG. 9. Any attempt to move lock 120 in that axial direction is prevented by abutment or contact between one or more of the finger end faces 150, 152, 154 or 156 and the adjacent shoulder 112. However, lock 120 can be moved to the left as viewed in FIG. 9. The inner surface 162 of lock body 122 is slidable or moveable along the annular transaction surfaces 116 as lock body 122 is moved in a leftward axial direction as viewed in FIG. 9. During such movement, the fingers 140, 142, 144 and 146 are flexed radially outwardly as they move along the ramp surface 114 of the detent formation. This continues until the finger ends pass over the annular transition surface 116 whereupon the fingers flex back into the next detent formation. At this point, the force adjusting mechanism is locked in position until lock 120 is again moved another step to the left as described. In the foregoing mode of operation, each finger moves in a manner similar to that of a living hinge.

Thus, the foregoing arrangement of co-operating structures on shaft 100 and lock 120 allow for a unidirectional ratchet movement of lock 120 on shaft 100. As a result, lock 120 may be advanced one step at a time, in one direction only, to compress the spring of an orthodontic appliance to apply force in a stepwise manner to one or more teeth in a patient's dental arch. Such movement of lock 120 along shaft 100 is effected manually, using an instrument in a manner which will be described, and the annular shoulder 130 facilitates engagement between such instrument and the lock body 122.

By way of example, in an illustrative force adjusting mechanism, lock 120 can be of 316 stainless steel, the overall axial length between end 126 and the finger and faces 150, 152, 154, 156 of about 0.125 inch, the inner diameter of body portion 122 can be about 0.047 inch, the wall thickness of body portion and the fingers 140, 142, 144, 146 can be about 0.005 inch and each finger can have an axial length of about 0.035 inch. The foregoing is by way of example, for purposes of illustration, and lock 120 can have other shapes and dimensions and be of other materials such as plastic and combinations of metal and plastic.

Figure 11:
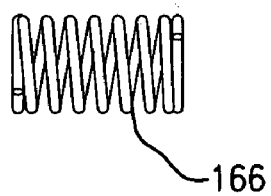
FIG. 11 is a perspective view of an orthodontic appliance spring associated with the force adjusting mechanism of the invention.

Orthodontic appliances in which the adjusting mechanism of the invention is employed commonly use coil springs which are compressed to apply force to one or more of the patient's teeth. Such springs 32, 34 and 86 were shown in the illustrative appliances of FIGS. 1 and 2. Such coil springs are conveniently useable with the force adjusting mechanism of the present invention, being readily fitted on the shaft and contacted on one end by the axial end surface of the lock. By way of further illustration, one such coil spring 166 is shown in FIG. 11.

Figure 12:
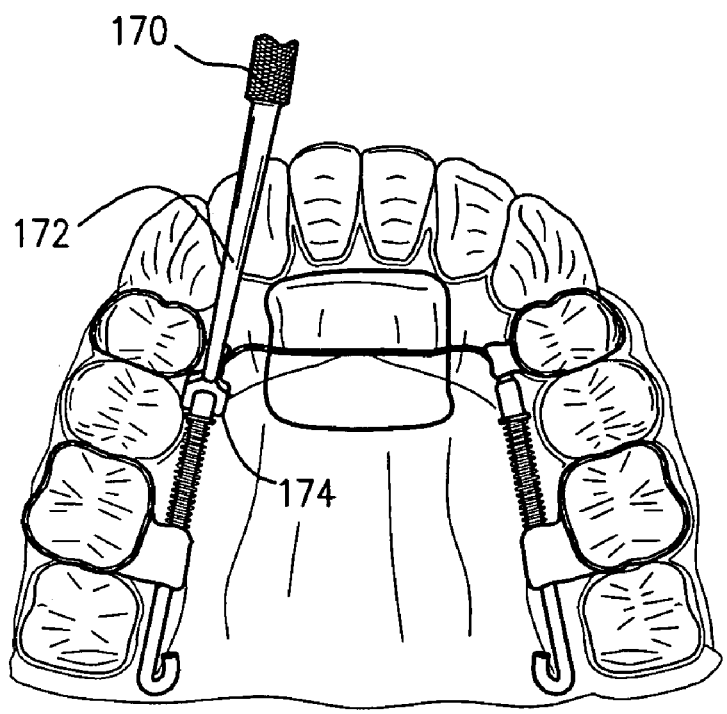
FIG. 12 is a perspective view showing an instrument for resetting the force adjusting mechanism of the invention in an orthodontic appliance.
Figure 13:
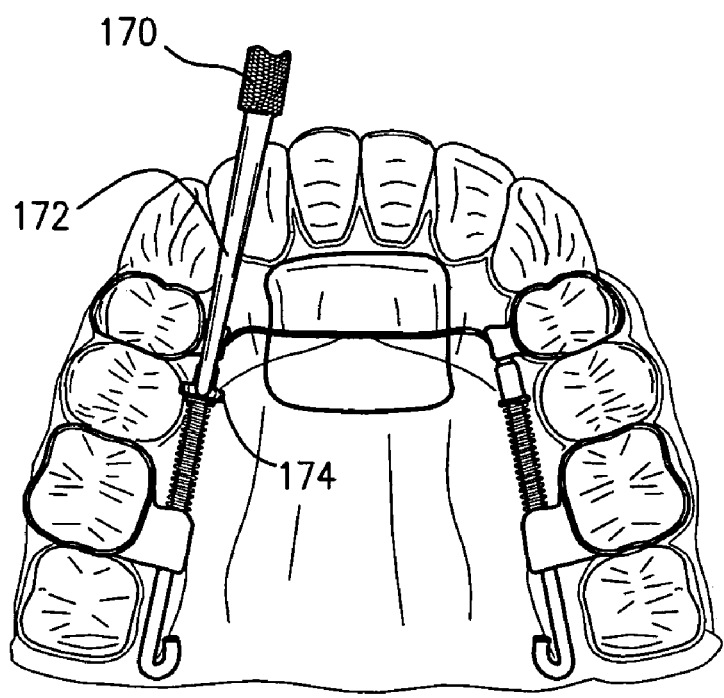
FIG. 13 is a view similar to FIG. 12 further illustrating use of the resetting instrument.

FIGS. 12 and 13 illustrate one form of instrument for manually moving the lock along the shaft in the force adjusting mechanism of the invention. The instrument 170 is in the form of a tool or implement having an elongated handle portion 172 and a lock-engaging portion 174 of the end thereof. Portion 174 is disposed at an angle to handle 172, which angle is substantial and approaching a right angle, and portion 174 is substantially U-shaped and dimensioned so that body portion 122 of lock 120 slidably fits within the legs of the U and so that the body of lock-engaging portion 174 can abut shoulder 130 on lock body 122. As a result, using a pushing or a pulling movement by manipulating handle 172 the patient or other person can advance the lock 122 incrementally along shaft 120 in a ratcheting and indexing manner as previously described.

By way of brief explanation, the appliance of the type shown in FIGS. 12 and 13 applies force to the rear molars 180, 182 and in that respect is similar to appliance 10 illustrated in FIG. 1. However, the appliance of FIGS. 12 and 13 is anchored to front molars 184 and 180 by way of bands 188 and 190, respectively, In addition, the appliance is supported by a plate 192 of plastic or like material contacting the palatal region of the patient's mouth. A frame member secured in plate 192 is joined at opposite ends through solder junctions 196 and 198, respectively, to bands 188 and 190, respectively, As in the appliance 10 of FIG. 1, the force adjusting mechanism of the invention is provided in duplicate, one for adjusting the force applied to each molar 180 and 182, and in this illustration each force adjusting mechanism includes a shaft and lock identical to those shown and described in FIGS. 3–10. Thus, one end of shaft 100' is connected to junction 196 and the other end extends through spring 202 and through a boss 204 on the lingual side of band 206. Lock 120' is movable in a unidirectional ratcheting manner along shaft 100' to compress spring 202 to apply force in a step-wise manner to the molar tooth 180. Similarly, one end of shaft 100" is connected to junction 198 and the other end extends through spring 208 and through a boss 210 on the lingual side of band 212. Lock 120" is movable in a unidirectional ratcheting manner along shaft 100" to compress spring 208 to apply force in a stepwise manner to the-molar teeth 182.

Figure 14:
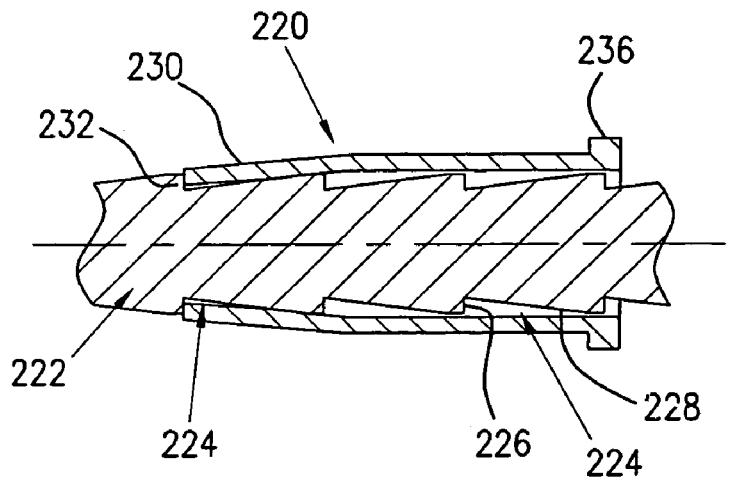
FIG. 14 is a fragmentary longitudinal sectional view illustrating an alternative form of lock and shown in position on the shaft of the force adjusting mechanism of the invention.

FIG. 14 shows an alternative form of lock for use in the force adjusting mechanism of the invention. Lock 220 is shown on a shaft 222 which is similar to shaft 100 of FIGS. 3–7 including a series of detent formations 224 each generally frustoconical in shape defining an annular shoulder 226 and an annular ramp-like surface 228. Lock 220 resembles lock 120 at FIGS. 8–10 in that it is in the form of a hollow cylindrical body. However, instead of having a plurality of fingers at one end, lock 220 has a continuous, slightly inwardly tapering portion 230 terminating in a continuous axial end face 232. Lock 220 is shown in FIG. 14 with axial end face 232 abutting a shoulder of one of the detent formations on shaft 222. Thus lock 220 cannot be moved any further to the left as viewed in FIG. 14. However, lock 220 can be moved along shaft 222 to the right as viewed in FIG. 14. The inner surface of the tapering portion 230 flexes outwardly as it is moved along the ramp surface 28 of the detent formation. This continues until the end face 234 of portion 230 passes beyond the ramp surface where upon portion 230 flexes back into the next detent formation. The material of lock 220, metal or plastic, would be selected to provide the necessary degree of flexure and spring-back of the tapering portion 230 to accomplish the foregoing action. Lock 220 can be provided with a formation in the form of annular rim 236, for engagement by a manually operated implement, such as instrument 170 shown in FIGS. 12 and 13 to move lock 20 along shaft 222.

Figure 15A:
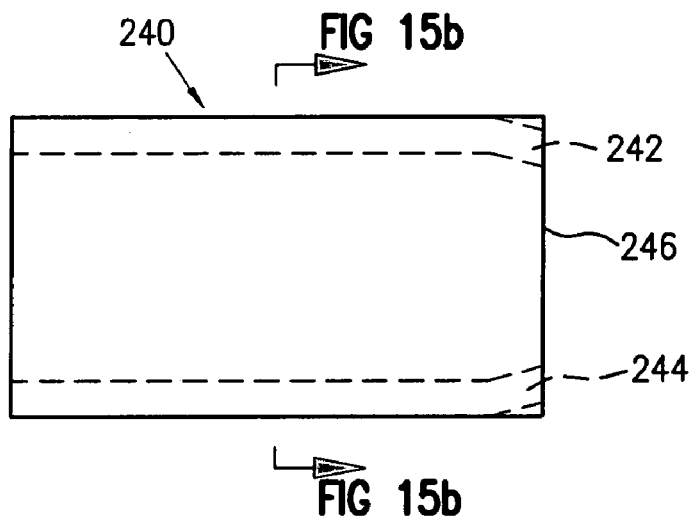
FIG. 15A is a side elevational view illustrating another alternative form of lock.
Figure 15B:
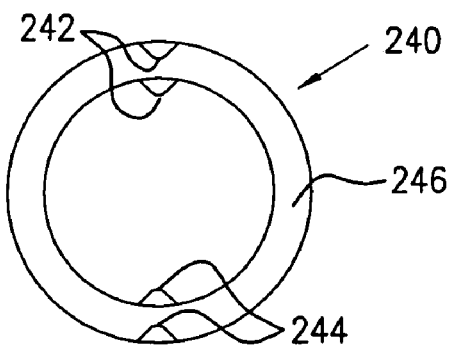
FIG. 15B is an end elevational view thereof.

FIGS. 15A and 15B show an alternative form of lock comprising a hollow cylindrical body 240 provided with a pair of radially opposite dimple-like projections 242, 244 at one axial end 246 of body 240. The projections 242, 244 extend radially inwardly so as to move into and out of detent formations on a shaft extending through body 240. The material and wall thickness of body 240 would be selected to provide the necessary degree of flexure/spring back of the projections 242, 244 so that they can move along the shaft detent formations in a manner analogous to the previously described locks.

Figure 16:
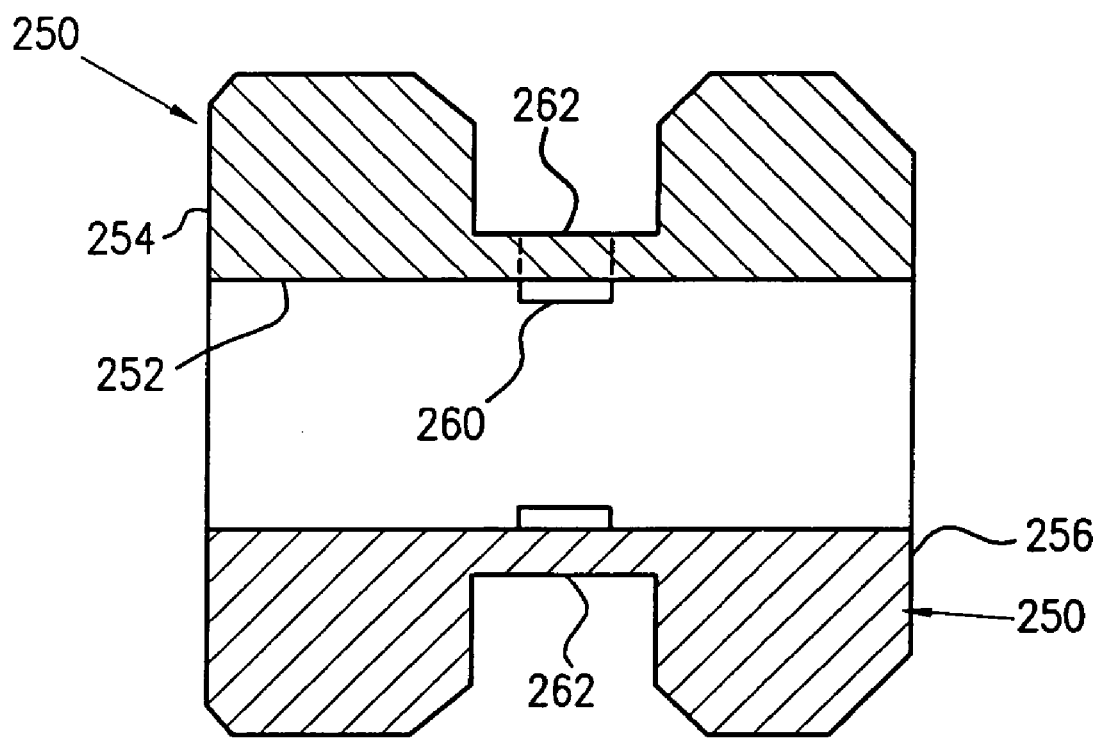
FIG. 16 is a longitudinal sectional view illustrating another alternative form of lock.

Another form of lock is shown in FIG. 16 and comprises a hollow body 250, preferably of plastic, wherein the component which is movable into and out of the shaft detent formations is located on the inner surface 252 of body 250 and preferably substantially mid-way between the axial ends 254, 256 thereof. The component 260 comprises a radially inwardly extending formation which can be annular or continuous or which can be a series of separate formations at circumferential locations around inner surface 252. Body 250 has annular region 262 of reduced thickness in the region of component 260 to facilitate its flexing movement into and out of the shaft detent formations as body 250 is moved along the shaft on which it is positioned in a manner analogous to the previously described locks.

Figure 17:
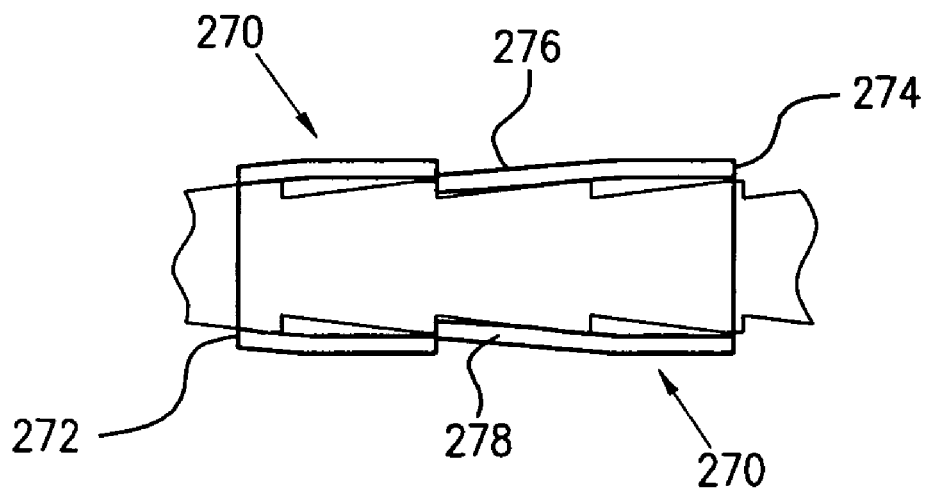
FIG. 17 is a longitudinal sectional view illustrating another alternative form of lock.

Another form of lock is shown in FIG. 17 and comprises a hollow body 270 wherein, like the lock of FIG. 16, the component which is movable into and out of the shaft detent formations is located preferably substantially midway between the axial ends 272, 274 thereof. However, in this embodiment, the component comprises one or more sections of the wall of body 270 which extend radially inwardly. In the lock shown in FIG. 17 there are two such sections 276 and 278. The wall thickness of body 270, together with the material thereof, facilitate the flexing movement of wall sections 276, 278 into and out of the shaft detent formations as they move along those formations in a manner analogous to the previously described locks.

Figure 18:
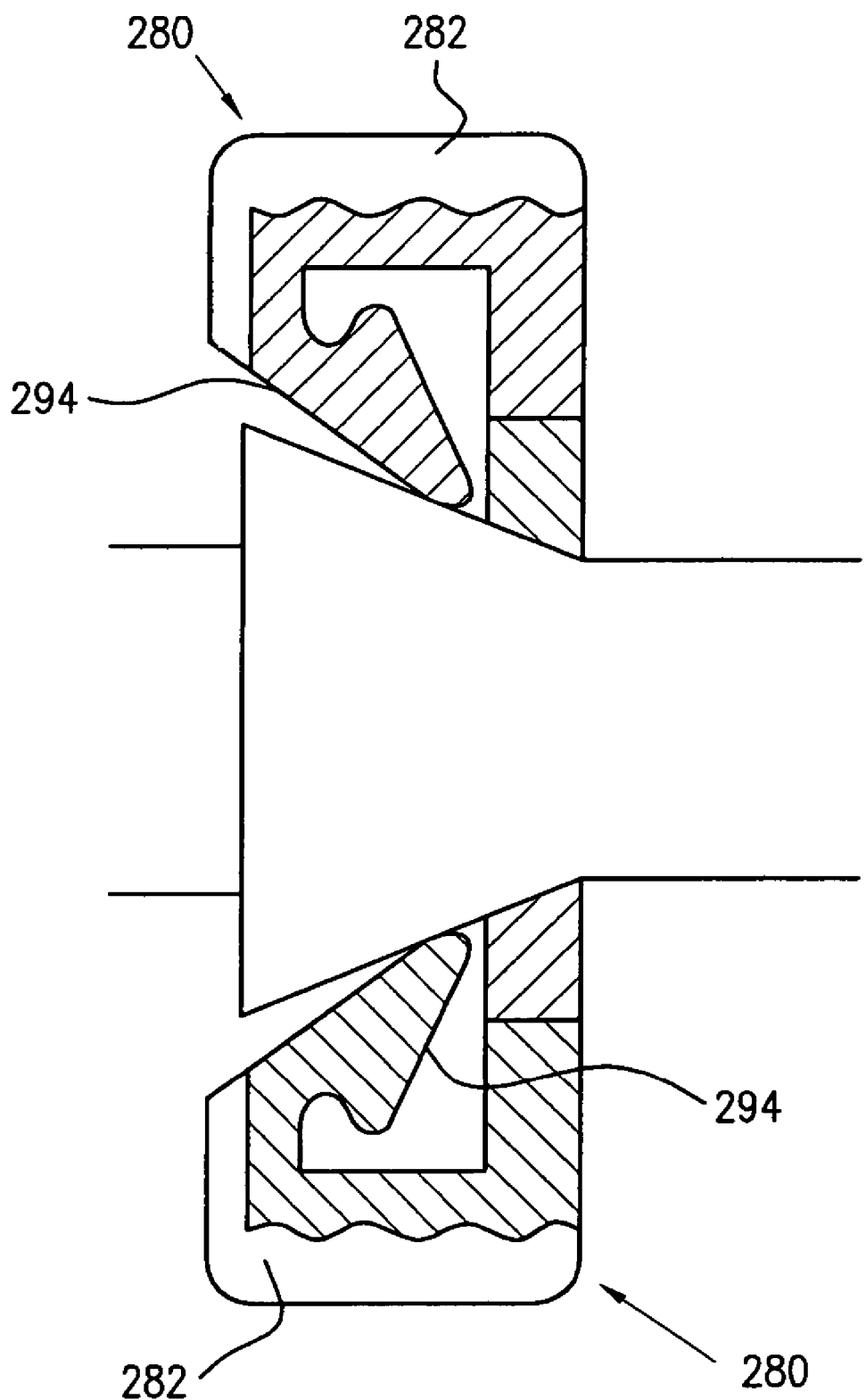
FIG. 18 is a longitudinal sectional view showing another alternative form of lock.

Another form of lock 290 is shown in FIG. 18 and comprises a composite body of a metal, preferably stainless steel, housing 292 and an insert 294 of a different material such as plastic, for example Nylon, whereby the insert 294 moves into and out of the shaft detent formations in a manner analogous to the previously described locks.

Figure 19:
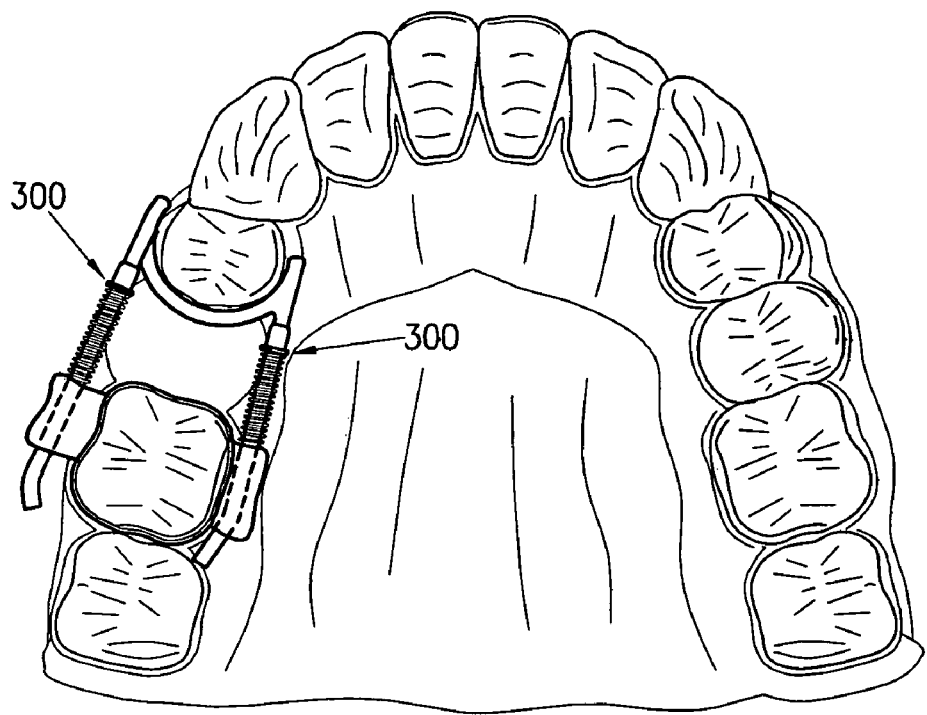
FIGS. 19 and 20 are perspective views showing additional forms of illustrative orthodontic appliances including the force adjusting mechanism of the invention.
Figure 20:
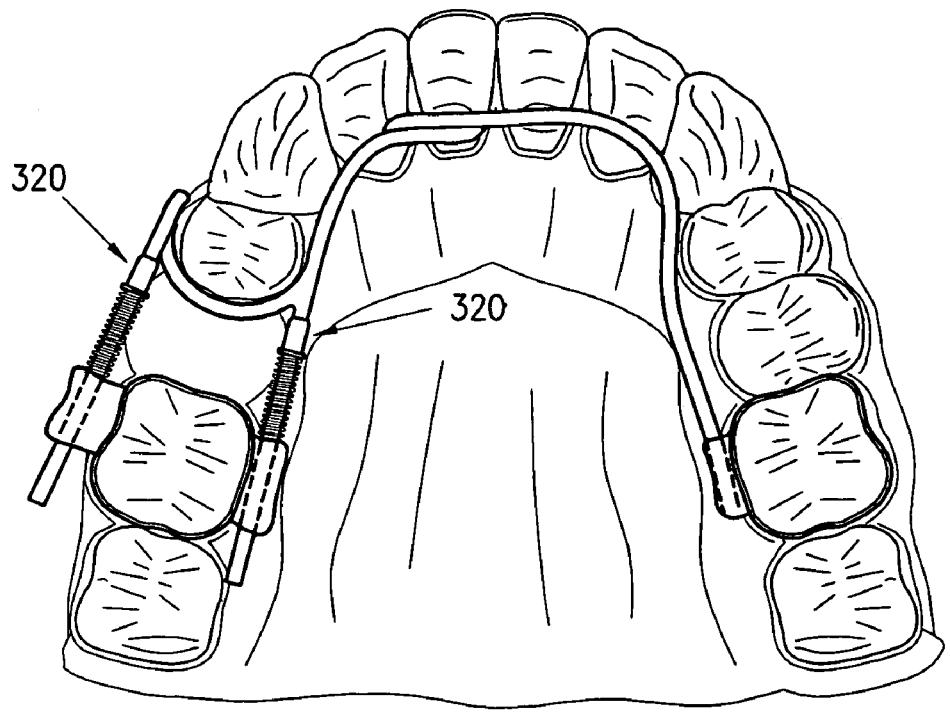

As previously mentioned, the particular appliances shown in FIGS. 1, 2, 12 and 13 are merely illustrative of many different types and varieties of orthodontic appliances in which the force adjusting mechanism of the invention is readily incorporated and highly effective. By way of further example, FIGS. 19 and 20 show two forms of space regainer type orthodontic appliance provided with the force adjusting mechanism of the invention. A regainer appliance functions to open spaces between teeth. The regainer shown in FIG. 19 functions to open space between the teeth with the band therearound and the abutment teeth. A pair of force adjusting mechanisms 300 is provided, each comprising shaft and lock for compressing the spring, the mechanisms 300 being identical, for example, to the mechanisms shown in the illustrative appliance of FIGS. 12 and 13. The regainer shown in FIG. 20 has the added anchorage of the lingual arch and functions to force the molar teeth back. A pair of force adjusting mechanisms 320 is provided, each comprising shaft and lock for compressing the spring, the mechanisms 320 being identical, for example, to the mechanisms shown in the illustrative appliance of FIGS. 12 and 13.

It is therefore apparent that the invention accomplishes its intended objectives. While embodiments of the invention have been described in detail, that has been done for the purpose of illustration, not limitation.

The invention claimed is:

1. A force adjusting mechanism for an orthodontic appliance located in association with a patient's dental arch and including spring means for applying force to one or more of the patient's teeth, the force adjusting mechanism comprising:
   a) a shaft operatively coupled at opposite ends between a first portion of the appliance which is anchored in the patient's dental arch and a second portion of the appliance including the spring means which applies force to one or more of the patient's teeth;

b) a lock movable along the shaft to compress the spring between the lock and the second portion of the appliance; and c) co-operating structures on the shaft and on the lock to provide a unidirectional ratchet movement of the lock along the shaft;

d) so that the lock may be advanced one step at a time in one direction only to compress the spring to apply force in a stepwise manner to one or more of the patient's teeth.

2. The force adjusting mechanism according to claim 1, wherein the co-operating structures comprise a series of successive detent formations along an outer surface of the shaft and a component on the lock movable into and out of the detent formations on the shaft.

3. The force adjusting mechanism according to claim 1, wherein the lock has a formation thereon for engagement by a manually operated instrument for moving the lock along the shaft.

4. The force adjusting mechanism according to claim 2, wherein the detent formations are defined by an axial series of substantially frusto-conical formations each having a ramp-like surface and providing a series of axially spaced-shoulders.

5. The force adjusting mechanism according to claim 4, wherein the lock component comprises one or more generally axially extending fingers which flex inwardly to be received with a corresponding shoulder and to ride along a corresponding ramp-like surface during the unidirectional ratchet movement of the lock along the shaft.

6. A kit for providing a force adjusting mechanism for an orthodontic appliance which applies spring force to one or more of a patient's teeth, the kit comprising:

a) a shaft having opposite ends for operative coupling between first and second portions of the appliance and a section between the ends having a series of successive detent formations therealong; and b) a lock movable along the shaft section and having a component movable into and out of the detent formations as the lock moves along the shaft section to provide a unidirectional ratchet movement of the lock along the shaft section;

c) so that the lock may be advanced manually one step at a time in one direction only to compress a spring to apply force in a stepwise manner to one or more of a patient's teeth.

7. A kit according to claim 6, further including a manually operated instrument having a formation thereon for engaging the lock to effect movement to the lock along the shaft section.

8. A kit according to claim 6, further including one or more springs for placement on the shaft to be compressed by the lock.

9. A method for adjusting force applied by an orthodontic appliance located in association with a patient's dental arch and including spring means for applying force to one or more of the patient's teeth, the method comprising:

a) providing in the appliance a force adjusting mechanism comprising a shaft operatively coupled at opposite ends between a first portion of the appliance which is anchored in the patient's dental arch and a second portion of the appliance including the spring means which applies force to one or more of the patient's teeth and a lock movable along the shaft to compress the spring means between the lock and the second portion of the appliance, there being co-operating structures on the shaft and on the lock to provide a unidirectional ratchet movement of the lock along the shaft; and b) manually advancing the lock one step at a time in one direction only to compress the spring to apply force in a stepwise manner to one or more of the patient's teeth.

10. The force adjusting mechanism according to claim 8, wherein the step of manually advancing the lock is performed by a manually operated instrument engaging the lock.

* * * * *